United States Patent [19]
Loveall

[11] Patent Number: 5,800,572
[45] Date of Patent: Sep. 1, 1998

[54] ARM SOCKET AND ATTACHED HAND PROSTHESIS

[76] Inventor: William H. Loveall, R.R. 1, Box 149A, Rutledge, Mo. 63563

[21] Appl. No.: 653,191

[22] Filed: May 24, 1996

[51] Int. Cl.$^6$ .................................. A61F 2/56; A61F 2/80
[52] U.S. Cl. .................... 623/63; 623/57; 623/33
[58] Field of Search .................... 623/64, 63, 57, 623/58, 33, 59; 601/5, 33, 40; 602/22

[56] References Cited

U.S. PATENT DOCUMENTS

| | | |
|---|---|---|
| Re. 15,006 | 12/1920 | Lawrence . |
| 45,876 | 1/1865 | Stoffel ............................ 623/63 |
| 104,994 | 7/1870 | Pingree . |
| 469,115 | 2/1892 | Boardman . |
| 908,881 | 1/1909 | Nelson ............................ 623/59 |
| 1,192,244 | 7/1916 | Tucker ............................ 623/59 |
| 1,338,155 | 4/1920 | Pringle et al. ................... 623/63 |
| 1,344,357 | 6/1920 | Shirer . |
| 1,885,138 | 11/1932 | Pilson . |
| 2,549,716 | 4/1951 | Simpson ....................... 623/58 X |
| 2,669,728 | 2/1954 | Ritchie ............................ 623/33 |
| 3,520,002 | 7/1970 | Wellington . |
| 3,545,009 | 12/1970 | Colley . |
| 3,545,046 | 12/1970 | Colley . |
| 3,802,302 | 4/1974 | Bengtson . |
| 4,842,608 | 6/1989 | Marx et al. . |
| 4,865,613 | 9/1989 | Rizzo . |
| 4,990,162 | 2/1991 | LeBlanc et al. . |
| 5,464,444 | 11/1995 | Farquharson et al. . |

FOREIGN PATENT DOCUMENTS

| | | | |
|---|---|---|---|
| 77606 | 8/1919 | Austria ......................... | 623/57 |
| 1683 | 7/1877 | Germany ....................... | 623/57 |
| 308667 | 10/1918 | Germany ....................... | 623/57 |
| 308668 | 10/1918 | Germany ....................... | 623/57 |
| 391185 | 3/1924 | Germany ....................... | 623/57 |
| 541216 | 8/1957 | Italy ............................... | 623/57 |
| 543396 | 1/1977 | U.S.S.R. ......................... | 623/57 |
| 1253643 | 8/1986 | U.S.S.R. ......................... | 623/57 |
| 157256 | 6/1921 | United Kingdom ........... | 623/57 |

*Primary Examiner*—David H. Willse
*Attorney, Agent, or Firm*—Grace J. Fishel

[57] ABSTRACT

An arm socket and attached hand prosthesis. The socket has a gate in an anterior wall making the socket easy to put on and allowing the user to adjust the pads on the interior of the socket to changes in the shape of the residuum or the amount of padding required over a scar or bony area. The hand prosthesis includes an artificial hand and a connector. The artificial hand has a stationary jaw and a movable jaw with a slidable ratchet bar connected at one end to the movable jaw for moving the movable jaw towards the stationary jaw and at the other to a cable, a pair of pawls in mesh with the ratchet bar for holding the movable jaw in selected position.

8 Claims, 4 Drawing Sheets

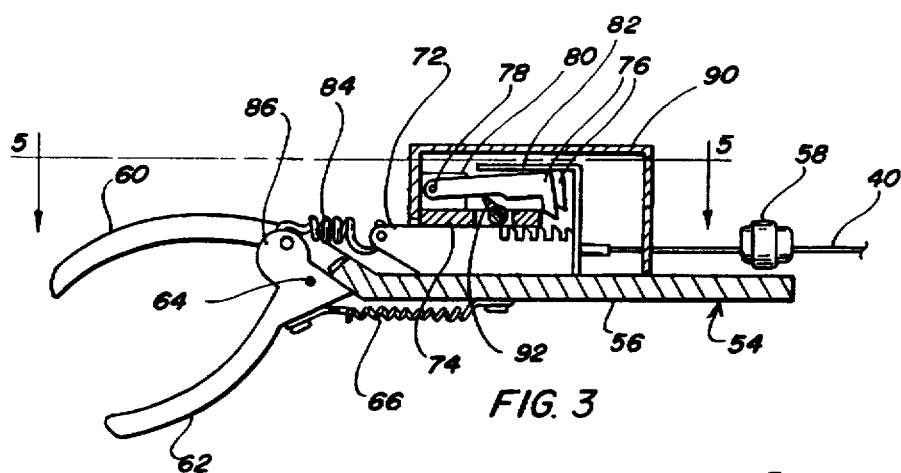
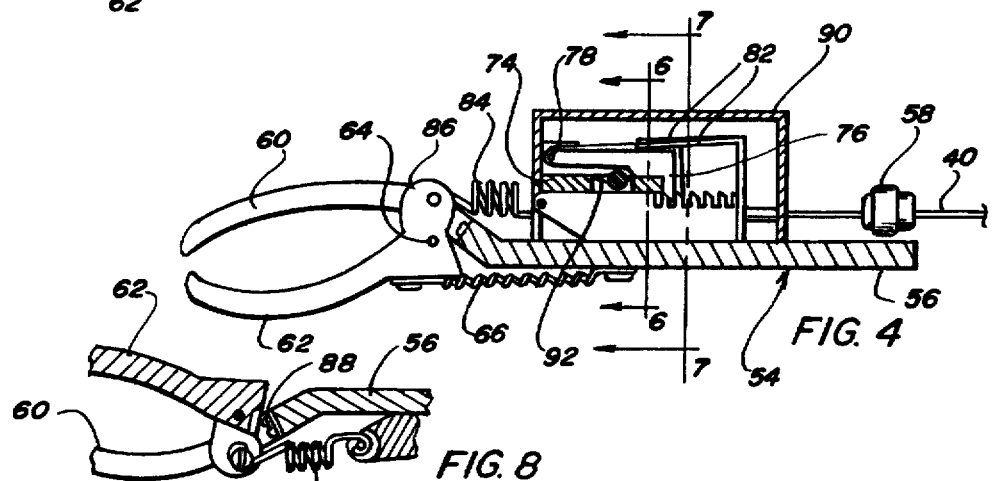
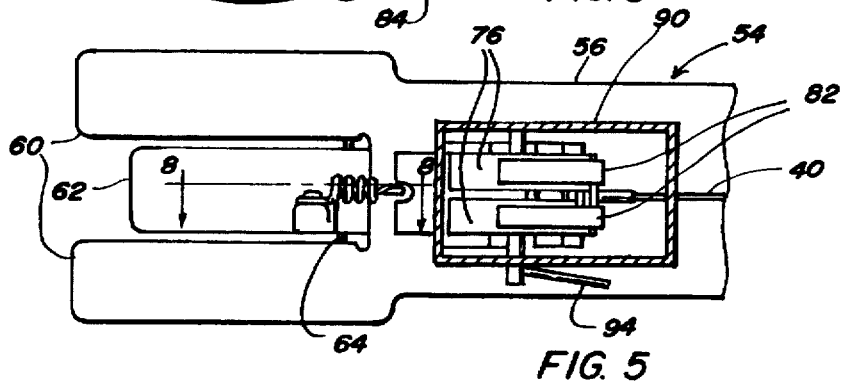
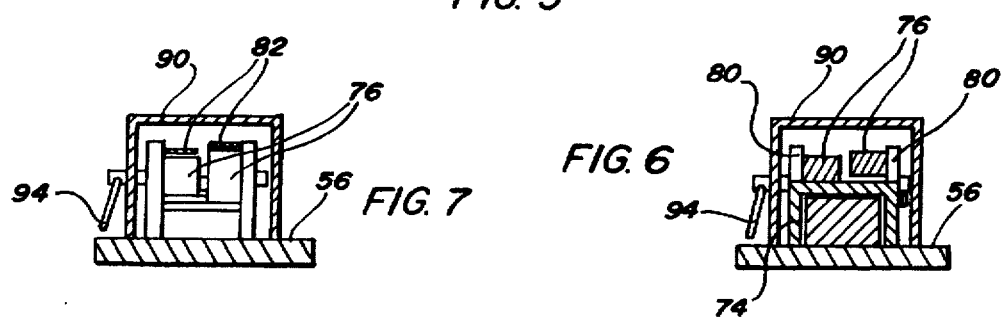

ARM SOCKET AND ATTACHED HAND PROSTHESIS

BACKGROUND OF THE INVENTION

1. Field of the Invention

The present invention relates to an improved arm socket and attached hand prosthesis, specifically designed to meet the requirements of amputees doing metal and construction work but having general utility.

2. Brief Description of the Prior Art

Arm sockets are made complementary in shape to the patient's limb stump with pads provided to secure a definitive fit. The pads in a typical arm socket are not accessible for adjustment by the patient. One of the problems encountered in using an arm socket is that the patient's limb stump changes shape due to pressure exerted thereon; the padded socket, however, does not change resulting in a poorly fitting and uncomfortable artificial limb. Another problem with a typical arm socket regards the manner in which it is put on. In general, a patient places an elongated tubular member over the limb stump, the end of which member is threaded through a hole provided in a sidewall of the socket for that purpose. The patient pushes his arm into the open end of the socket while pulling on the tubular member which acts like a Chinese finger torture compressing the residuum. The stump is thus pushed and pulled into the prosthesis.

A hook has been the classic prosthesis for the amputee of a hand or forearm. Typically the hook or, more specifically, a split hook, consists of two hook sections joined at one end by a pivot. The terminal ends of the two sections are maintained in contact with each other by rubber bands wrapped around the two sections near the pivot point. A lever mounted on one of the hook sections and connected to a cable attached to the upper arm or shoulder is used to open the hook. The hook provides maximum visibility to the patient of the object being picked up. The hook is also durable and the force needed to open it is relatively small but its clamping action has been limited by the strength of the rubber bands. For amputees who want to do metal and construction work, presently available hand prostheses do not provide enough gripping force. Another requirement for metal and construction work is that the hand prosthesis be adjustable so that the object, either a workpiece or a tool, can be held at different angles during the required operation. Cosmetic value of the prosthesis is of secondary concern. Cost, however, is of great concern. There are a number of sophisticated prosthetic devices for use by amputees that are driven, or at least assisted, by electrical, myoelectrical and/or pneumatic means. Most of these devices, however, are very expensive to manufacture and to keep in repair.

SUMMARY OF THE INVENTION

In view of the above, it is an object of the present invention to provide an arm socket that is easy to put on and that can be fitted by the user to changes in the shape of the residuum or the amount of padding required over a scar or bony area. It is another object to provide an artificial hand for firmly grasping a tool or a workpiece. It is also an object to provide an arm socket and attached hand prosthesis that is rugged, relatively inexpensive and simple to construct and maintain. Other objects and features of the invention will be in part apparent and in part pointed out hereinafter.

In accordance with the invention, a socket for a residuum of an arm has a shell formed to essentially match the contour of the residuum. The shell has an open proximal end and a closed distal end. A posterior wall and an anterior wall are attached to the closed end, as are opposed medial and lateral walls. Medial and lateral walls merge into the posterior and anterior walls to form a continuous sidewall. The shell has a lining of soft, compressible material disposed over at least a portion of an interior surface of the shell. A gate is formed in the anterior wall, opening the shell along its open proximal end and is hinged along either the medial or lateral walls. A fastener for securing the gate closed is provided along the medial or lateral wall opposite the hinged side of the gate. When the gate is open, the lining in the shell can be adjusted for changes in the shape of the residuum or the amount of padding required over a scar or bony area and the residuum can be easily slipped into the socket.

A hand prosthesis for attachment to the socket includes an artificial hand and a connector. The artificial hand has an elongated plate with a pair of jaws at one end. One of the jaws is movable toward the other to grasp an article therebetween. A slidable ratchet bar is mounted on the plate and is connected to the movable jaw for moving the movable jaw towards the other jaw. The ratchet bar has teeth and is connected to a shoulder operable cable. A pair of pawls are in mesh with the teeth of the ratchet bar, the pawls alternately serving as a catch while the other slides over one of the teeth in the ratchet bar. By movement of the shoulder operable cable, the wearer can firmly clamp the artificial hand on the article, which grip is maintained by the pawl in mesh with the ratchet bar.

The connector has a pair of telescoping sections, one of which is threaded at one end and the other of which has a collar which can be slid along the section. A compression bushing which can be slid along the section with the collar is provided on that section. The compression bushing is adapted to lock the sections in selected telescoped relationship when the collar is threaded on the section with the threads. The sections have attachment links on their ends opposite the ends where they are telescoped, one of said attachment links attaching the artificial hand the other of which attaching the socket. The angular relationship among the socket, connector and artificial hand is adjustable at the connecting links and through the telescoping sections.

The invention summarized above comprises the constructions hereinafter described, the scope of the invention being indicated by the subjoined claims.

BRIEF DESCRIPTION OF THE DRAWINGS

In the accompanying drawings, in which one of various possible embodiments of the invention are illustrated, corresponding reference characters refer to corresponding parts throughout the several views of the drawings in which:

FIG. 3 is a section taken along line 3—3 in FIG. 2 showing a movable jaw of the artificial hand in open position;

FIG. 4 is a view similar to FIG. 3 but wherein the movable jaw has moved towards closed position;

FIG. 5 is a section taken along line 5—5 in FIG. 3, on an enlarged scale with a portion broken away;

FIG. 6 is a section taken along line 6—6 in FIG. 4;

FIG. 7 is a section taken along line 7—7 in FIG. 4;

FIG. 8 is a section taken along line 8—8 in FIG. 5;

DETAILED DESCRIPTION OF THE INVENTION

Figures 1, 2:
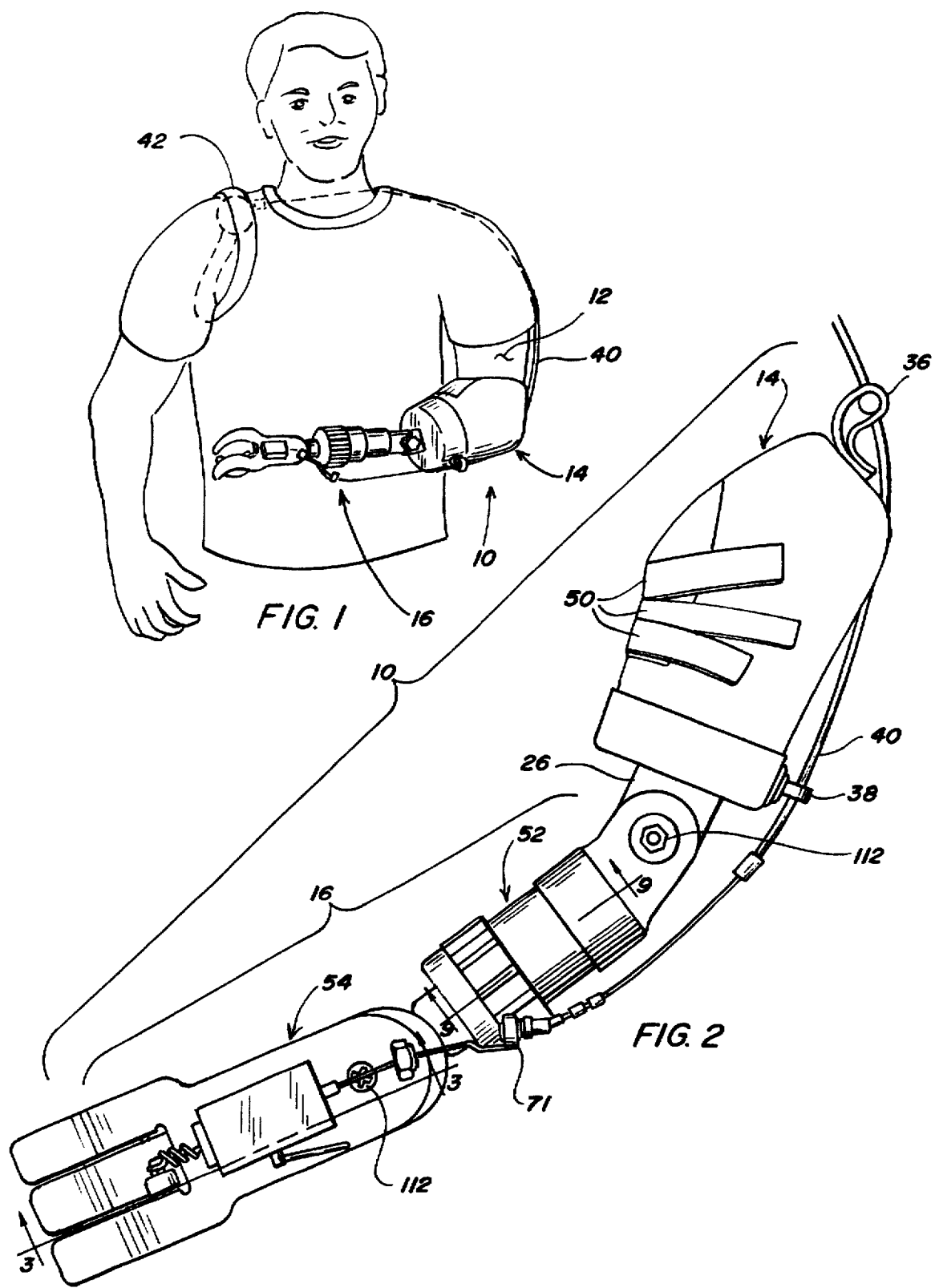
FIG. 1 is a view of an arm socket and hand prothesis in accordance with the present invention in use by an amputee.
FIG. 2 is a side elevation of the arm socket and hand prosthesis, the hand prosthesis composed of an artificial hand and a connector.
Figure 9:
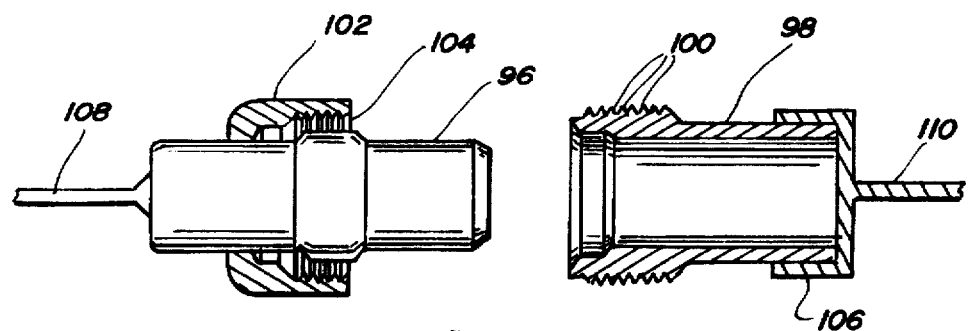
FIG. 9 is a section taken along line 9—9 in FIG. 2 showing the sections of the connector unassembled.
Figure 10:
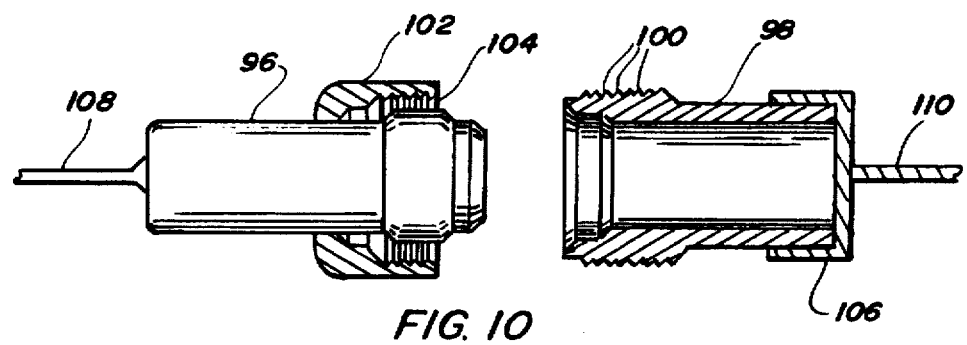
FIG. 10 is a section similar to FIG. 9 but wherein a compression bushing has been slid along one of the sections for adjusting the length of the connector by controlling the extent to which the sections telescope.
Figure 11:
FIG. 11 is a perspective view on an enlarged scale of the arm socket open with a residuum in process of being inserted.
Figure 12:
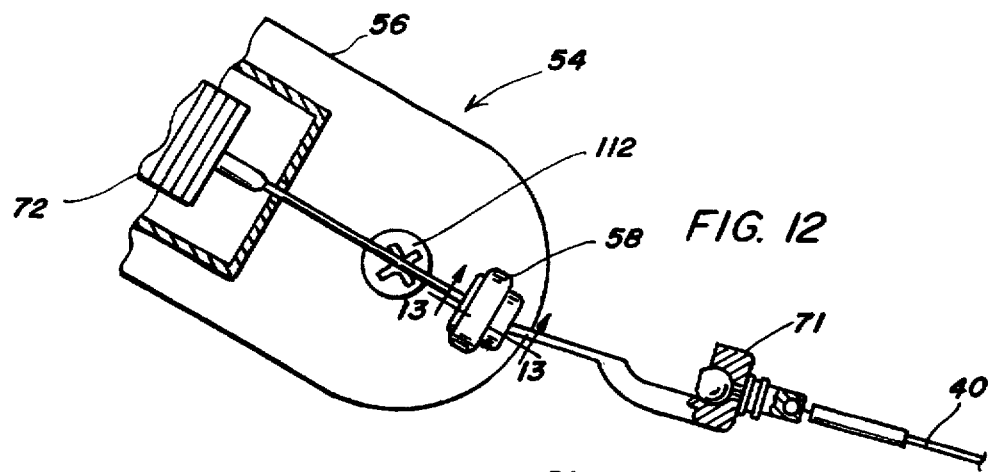
FIG. 12 is a plan view of a proximal end of the artificial hand showing its attachment to a cable.

Referring to the drawings more particularly by reference character, reference numeral 10 refers to a prosthetic device that replaces a missing hand. As illustrated in the drawings, the person affected is an amputee who has lost his entire hand and a portion of the arm below the elbow. Prosthetic device 10 is secured to the remaining portion of the radius and ulna (i.e., a residuum 12) and replaces the entire wrist and hand. It is to be understood, however, that all or any portion of the prosthetic device described herein is to be employed as circumstances require, including on malformed or injured limbs truncated above the elbow.

In major part, prosthetic device 10 includes a socket 14 and a hand prosthesis 16. Socket 14 has a rigid outer shell 18 defining a cavity for receiving residuum 12, essentially matching the contour thereof. Shell 18 has an open proximal end 20 and a closed distal end 22. The closed distal end 22 terminates in an end face normal to the axis of the shell. The end face is provisioned with means for attaching a hand prosthesis. When the hand prosthesis is a hook, the end face typically has a threaded receptacle (not shown) capable of receiving a threaded fastener attached to the base of the hook. For attachment of hand prosthesis 16, the end face is provisioned with a metal cap 24 on which is mounted an attachment link 26. For economy in fabrication, metal cap 24 may be offered in a range of standard sizes for attachment to shell 18 which may be custom fitted. Shell 18 further includes a posterior wall 28 and anterior wall 30 and opposing medial and lateral walls 32, 34, respectively, attached to closed end 22. Medial and lateral walls merge into posterior and anterior walls, forming a continuous sidewall that tapers progressively from proximal end 20 to distal end 22 such that the peripheral dimension of the shell is normally greater at the proximal end than it is at the distal end. Shell 18 may be outfitted with a loop 36 on its posterior wall 28 at proximal end 20 and an eye 38 at distal end 22 through which a cable 40 attached to a shoulder harness 42 may be threaded. Shoulder harness 42 and cable 40 are standard items, typically fitted to the wearer by a prosthetist.

While shell 18 is designed to fit residuum 12 closely, it cannot be fitted tight as there are natural daily variations in the volume of a living stump. Such fluctuations result from several causes, including system fluid shifts. At other times, it is necessary to change the thickness of the padding over scar and bony areas, which may become irritated. A lining of soft, compressible material is disposed over at least a portion of an interior surface of shell 18 forming pads 44. Particularly suitable material for pads 44 includes silicone rubber having the texture of muscle. The lining may have a sticky backing allowing pieces of it to be layered, permitting the thickness of pads 44 to be adjusted to suit variations in the shape of the residuum or the amount of padding required. Pads 44 are accessible for minor adjustments (as more particularly described below) so there is no need for the amputee to suffer a poorly fitting and uncomfortable artificial limb until it is adjusted by a prosthetist, or replaced.

A gate 46 is formed in anterior wall 30, opening proximal end 20 of the shell, and is hinged at 48 to the shell along one of medial or lateral walls 32, 34. Hinge 48 may take a variety of forms that are functionally equivalent to the hinge shown in the drawings. A fastener 50 such as a belt for securing gate 46 closed along the medial or lateral wall opposite the hinged side of the gate is provided. Belts 50 may be formed of material having weaving on one side which interlockingly adheres to the other side, for example VELCRO, one gender of which may be attached to gate 46 and the opposite gender of which may be attached to shell 18. By unfastening belts 50, gate 46 can be easily opened and closed, permitting ready access to pads 44 for adjustment of their thickness and placement and permitting easy insertion of residuum 12 into shell 18.

Figure 13:
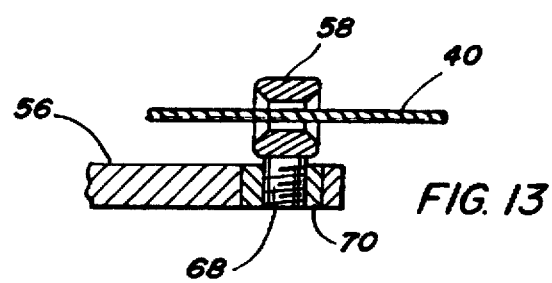
FIG. 13 is a section taken along line 13—13 in FIG. 12.
Figure 14:
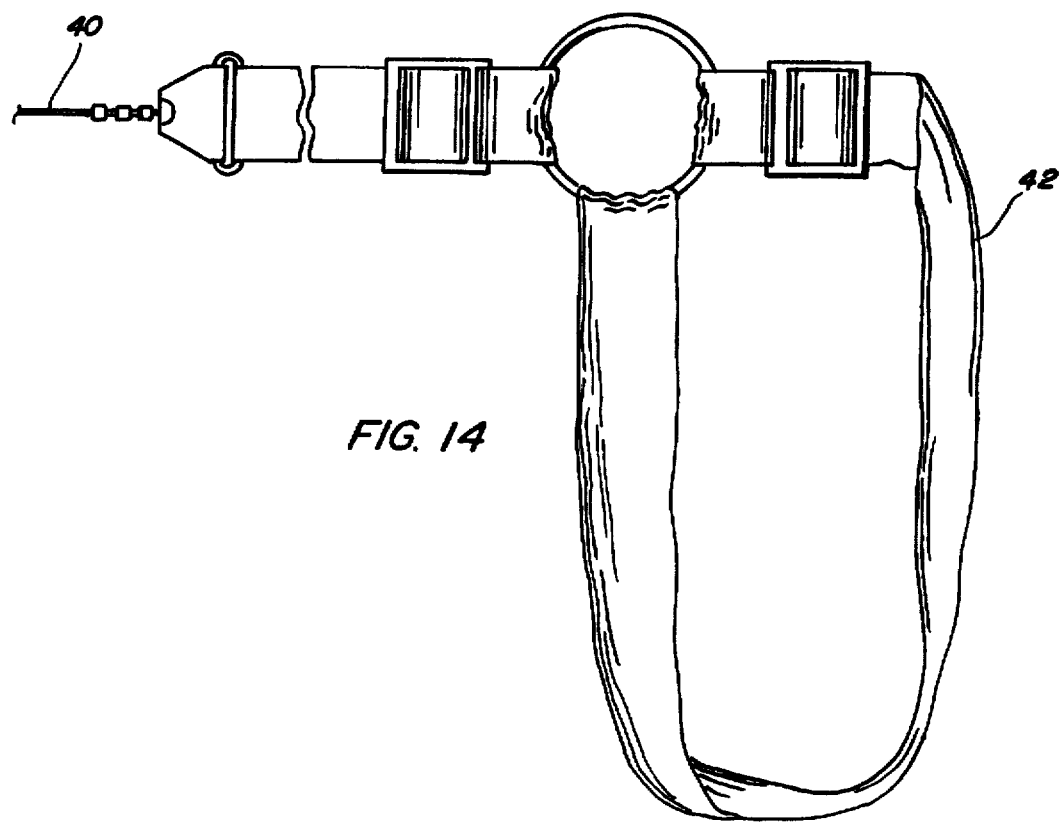
FIG. 14 is a plan view of a shoulder harness for pulling the cable attached to the artificial hand.

Hand prosthesis includes a connector 52 and an artificial hand 54. Artificial hand 54 has an elongated plate 56 with a swivel cable eye 58 at a proximal end and a stationary jaw 60 at a distal end. Stationary jaw 60 is bifurcated into curved fingers, spaced apart a distance equal to about the width of three fingers. A movable jaw 62 is pivoted at 64 between the fingers of stationary jaw 60, forming a curved thumb, interposed between the fingers, with the curvature of the fingers and thumb matching those of a relaxed human hand. Movable jaw 62 is biased toward open position by a spring 66. As shown in FIG. 13, swivel cable eye 58 is flared at both ends to avoid cutting cable 40. Swivel cable eye 58 is mounted on a threaded post 68 which turns on the threads of a bushing 70 provided in the proximal end of plate 56. A snap coupling 71 is provided in cable 40 adjacent swivel cable eye 58 for use when artificial hand 54 is detached from connector 52.

Spaced a distance from stationary jaw 60, a ratchet bar 72 is slidably mounted for rectilinear movement on elongated plate 56 in a guide 74 attached to the plate. A pair of pawls 76 are pivoted at 78 between ears 80 formed on guide 74. Springs 82 maintain pawls 76 in mesh with the teeth of ratchet bar 72, one end of the springs being attached to a proximal end of rachet bar 72 and the other end of which slides across the top of pawls 76. Each of pawls 76 alternately serve as a safety catch, while the other slides over a tooth of ratchet bar. A distal end of ratchet bar 72 is attached to one end of a spring 84, the opposite end of which is attached to an arm 86 connected at pivot 64 to (or integrally formed with) movable jaw 62. A proximal end of ratchet bar 72 is attached to cable 40 passing through swivel eye 58. As best seen in FIG. 8, a bumper 88 is provided on stationary jaw 60 adjacent the hinge point of movable jaw 62 for stopping movable jaw 62 from crushing an object grasped between the jaws. A protective housing 90 for ratchet bar 72 and pawls 76 is provided on elongated plate 56 through which the ends of cable 40 and spring 84 pass. Pawls 76 may be disengaged from ratchet bar 72 by upward pressure of a butterfly 92 attached to a lever 94 accessible through protective housing 90.

Connector 52 includes a pair of telescoping tubular sections 96, 98, one of which is threaded at 100 for engagement with the threads of a collar 102 carried by the other. The extent that sections are telescoped is controlled by a compression bushing 104 which can be slid along section 96 when collar 102 is unthreaded but which fixes the collar on section 96 when it is screwed on threads 100. A distal end of section 96 and a proximal end of section 98 are capped at 106, terminating with attachment links 108, 110, respectively, connected to the cap on centerline with the long axis of the sections. Collar 102 is loose on section 96 so that the angular relationship of attachment links 108, 110 can be changed, thereafter locking sections 96, 98 in selected relationship as the collar is tightened on the threads.

Connector 52 serves as an artificial wrist, connecting socket 14 to artificial hand 54, through attachment link 110 at the proximal end of section 98 connected with a fastener 112 to the distal end of attachment link 26 on shell 18. Similarly, attachment link 108 at the distal end of section 96 is connected with a fastener 112 to the proximal end of plate 56. The angular relationship of the connector to socket 14 and artificial hand 54 can be adjusted at fasteners 112. Connector 52 may also be used as an attachment site for a variety of implements other than artificial hand 54, as for example cable operated hooks, scissors, pliers, etc.

In use, prior to putting on socket 14, cable 40 is connected to shoulder harness 42 and passed through loop 36 and eye 38 on socket 14 with snap coupling 71 open. Artificial hand 54 is attached to connector 52 and connector 52 is attached to socket 14. A user then puts on shoulder harness 42, which along with cable 40 has been fitted to him, and inserts residuum 12 into socket 14. This is easily accomplished by opening gate 46 prior to inserting residuum 12 into the cavity of shell 18. Gate 46 is shut and strapped closed with fasteners 50. If socket 14 feels uncomfortable, the wearer can release the belts, open the gate and remove his arm. He can then make such adjustments as are necessary to pads 44. Once a comfortable fit has been established, gate 46 is strapped closed and the end of cable 40 that passes through swivel cable eye 58 is attached to the end of cable 40 that passes through eye 38 with snap coupling 71. Collar 102 and fasteners 112 may be loosened so that connector 52 and artificial hand 54 are placed in the desired angular relationship.

When the user wants to grip an object in artificial hand, he pulls on cable 40 by twisting his shoulder in shoulder harness 42. As cable 40 is pulled, ratchet bar 72 is moved in the direction of the proximal end of plate 56, causing movable jaw 62 to move toward stationary jaw 60. Closure of movable jaw 62 beyond a set point is prevented by bumper 88. As ratchet bar 72 is moved, pawls 76 keep it from slipping back and releasing the tension on movable jaw 62; thus the force of the grip is maintained without requiring the user to continue to pull on cable 40 with harness 42. When the user wants to release his grip on the object, lever 94 is rotated, causing butterfly 92 to disengage pawls 76 from rachet bar 72. As pawls 76 are released, ratchet bar 72 can slide in the direction of the distal end of plate 56, causing movable jaw 62 to move away from stationary jaw 60 and releasing the grip on the object.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A socket for a residuum of an arm with a below elbow amputation comprising a shell formed to essentially match the contour of the residuum, said shell having an open proximal end, a closed distal end, a posterior wall and an anterior wall attached to the closed end and opposed medial and lateral walls, said medial and lateral walls attached to the closed end and merged into the posterior and anterior walls, a lining of soft, compressible material disposed over at least a portion of an interior surface of said shell, a gate formed in the anterior wall at the elbow, opening the shell along the proximal end and hinged along either the medial or lateral walls and a fastener for securing the gate closed along the medial or lateral wall opposite the hinged side of the gate whereby the lining in the shell can be adjusted with the gate open and the residuum of an arm, including the elbow, easily slipped into the socket.

2. The socket of claim 1 wherein the socket has a central axis and the closed distal end terminates in a face normal to the central axis of the socket, a cap with a connecting link attached thereto mounted on said face.

3. The socket of claim 1 wherein the lining is made of silicone rubber having a texture similar to muscle.

4. A prosthetic device comprising a socket, a connector and an artificial hand, said socket comprising a shell formed to essentially match the contour of a residuum, said shell having an open proximal end, a closed distal end, a posterior wall and an anterior wall attached to the closed end and opposed medial and lateral walls, said medial and lateral walls attached to the closed end and merged into the posterior and anterior walls, a lining of soft, compressible material disposed over at least a portion of an interior surface of said shell, a gate formed in the anterior wall, opening the shell along the proximal end and hinged along either the medial or lateral walls; and, a fastener for securing the gate closed along the medial or lateral wall opposite the hinged side of the gate whereby the lining in the shell can be adjusted with the gate open and the residuum of an arm easily slipped into the socket;

said artificial hand having an elongated plate with a pair of jaws at one end, one of said jaws being movable toward the other to grasp an article therebetween, the other of said jaws being stationary, a slidable ratchet bar mounted on the plate and connected to the movable jaw, said ratchet bar having teeth and being connected to a shoulder operable cable and a pair of pawls in mesh with the teeth of the ratchet bar, one of said pawls alternately serving as a catch while the other slides over one of the teeth of the ratchet bar whereby by movement of the shoulder operable cable, a wearer can firmly clamp the artificial hand on the article, which grip is maintained by the pawl in mesh with the ratchet bar;

said connector having a pair of telescoping sections, one of which is threaded at one end and the other of which has a collar and a compression bushing which can be slid along the section, said compression bushing locking the sections in selected telescoped relationship when the collar is threaded on the section with threads, said sections having attachment links at ends opposite the ends where they are telescoped, fasteners for connecting one of the attachment links to the artificial hand, fasteners for connecting the other of attachment links to an attachment link on the socket whereby the angular relationship among the socket, connector and artificial hand is adjustable at the attachment links and through the telescoping sections.

5. The prosthetic device of claim 4 wherein the socket has a central axis and the closed distal end terminates with a face normal to the central axis of the socket, a cap with the attachment link for attachment to one of the attachment links on the connector is mounted on said face.

6. The prosthetic device of claim 5 wherein the stationary jaw is bifurcated into curved fingers, wherein the movable jaw is pivoted between the fingers of the stationary jaw, forming a curved thumb, interposed between the fingers.

7. The prosthesis device of claim 6 wherein a bumper is provided on the stationary jaw for stopping the movable jaw from crushing an object grasped between the jaws.

8. The prosthesis device of claim 7 wherein springs are attached to the ratchet bar for keeping the pawls in mesh with the teeth of the ratchet bar.

* * * * *